(12) United States Patent
Gonzalez Marín et al.

(10) Patent No.: US 9,879,284 B2
(45) Date of Patent: Jan. 30, 2018

(54) METHOD FOR OBTAINING NATURAL EXTRACTS, OLEORESINS, CONDIMENTS, COLORANTS, FLAVORING SUBSTANCES AND AROMAS FROM AROMATIC PLANT SUBSTANCES, ALFALFA, FLOWERS WITH PIGMENTS, AND VEGETABLES

(76) Inventors: Alfonso José Gonzalez Marín, Murcia (ES); Carmelo González Marín, Murcia (ES)

( * ) Notice: Subject to any disclaimer, the term of this patent is extended or adjusted under 35 U.S.C. 154(b) by 176 days.

(21) Appl. No.: 13/235,108

(22) Filed: Sep. 16, 2011

(65) Prior Publication Data

US 2012/0237970 A1    Sep. 20, 2012

(30) Foreign Application Priority Data

Oct. 28, 2010 (ES) .................................. 201031585
May 26, 2011 (ES) .................................. 201130867

(51) Int. Cl.
*C12P 1/00* (2006.01)
*A23L 27/10* (2016.01)
*A23L 5/43* (2016.01)
*A23L 33/105* (2016.01)

(52) U.S. Cl.
CPC ................. *C12P 1/00* (2013.01); *A23L 5/43* (2016.08); *A23L 27/10* (2016.08); *A23L 33/105* (2016.08)

(58) Field of Classification Search
None
See application file for complete search history.

(56) References Cited

U.S. PATENT DOCUMENTS

| | | | |
|---|---|---|---|
| 2,863,805 A * | 12/1958 | Todd .............................. | 435/271 |
| 6,419,962 B1 * | 7/2002 | Yokoyama et al. .......... | 424/725 |
| 6,797,303 B2 * | 9/2004 | Zelkha et al. ................ | 426/431 |
| 7,691,417 B2 * | 4/2010 | Gray et al. .................... | 424/725 |
| 2003/0091704 A1 * | 5/2003 | Lee et al. ...................... | 426/250 |
| 2003/0175364 A1 * | 9/2003 | Newman et al. ............. | 424/725 |
| 2004/0131635 A1 * | 7/2004 | Colonat et al. .......... | 424/195.17 |
| 2008/0317920 A1 * | 12/2008 | Bouraoui et al. ............. | 426/392 |

FOREIGN PATENT DOCUMENTS

ES        482035 A1 *   2/1980

OTHER PUBLICATIONS

Salgado-Roman (Journal of Agricultural and Food Chemistry (2008), vol. 56, pp. 10012-10018).*
Mantzouridou (Journal of Agricultural and Food Chemistry (2006), vol. 54, pp. 2575-2581).*

* cited by examiner

*Primary Examiner* — Susan Hoffman
(74) *Attorney, Agent, or Firm* — Steve Hassid; Partners Law Group, Inc.

(57) ABSTRACT

A method for obtaining natural extracts, oleoresins, colorants flavors and aromas from aromatic plant substances, alfalfa, flowers with pigments, and vegetables, which includes washing the plant substances and vegetables, rinsing with water, milling and sifting the resulting product yielding a pulp phase and a cellulose phase. The pulp phase is transferred to fermentation tanks and a first centrifugation of the fermented pulp phase is then performed yielding two phases: phase (A) containing water, mineral salts and other water-soluble substances, with natural extracts, oleoresins, colorants, aromas and flavors and phase (B) in the form of a paste in which the moisture has been reduced to 50%, performing a second centrifugation of the mentioned phase (A), which causes the separation of natural extracts, oleoresins, colorants, aromas and flavors from the water and other water-soluble substances.

7 Claims, 1 Drawing Sheet

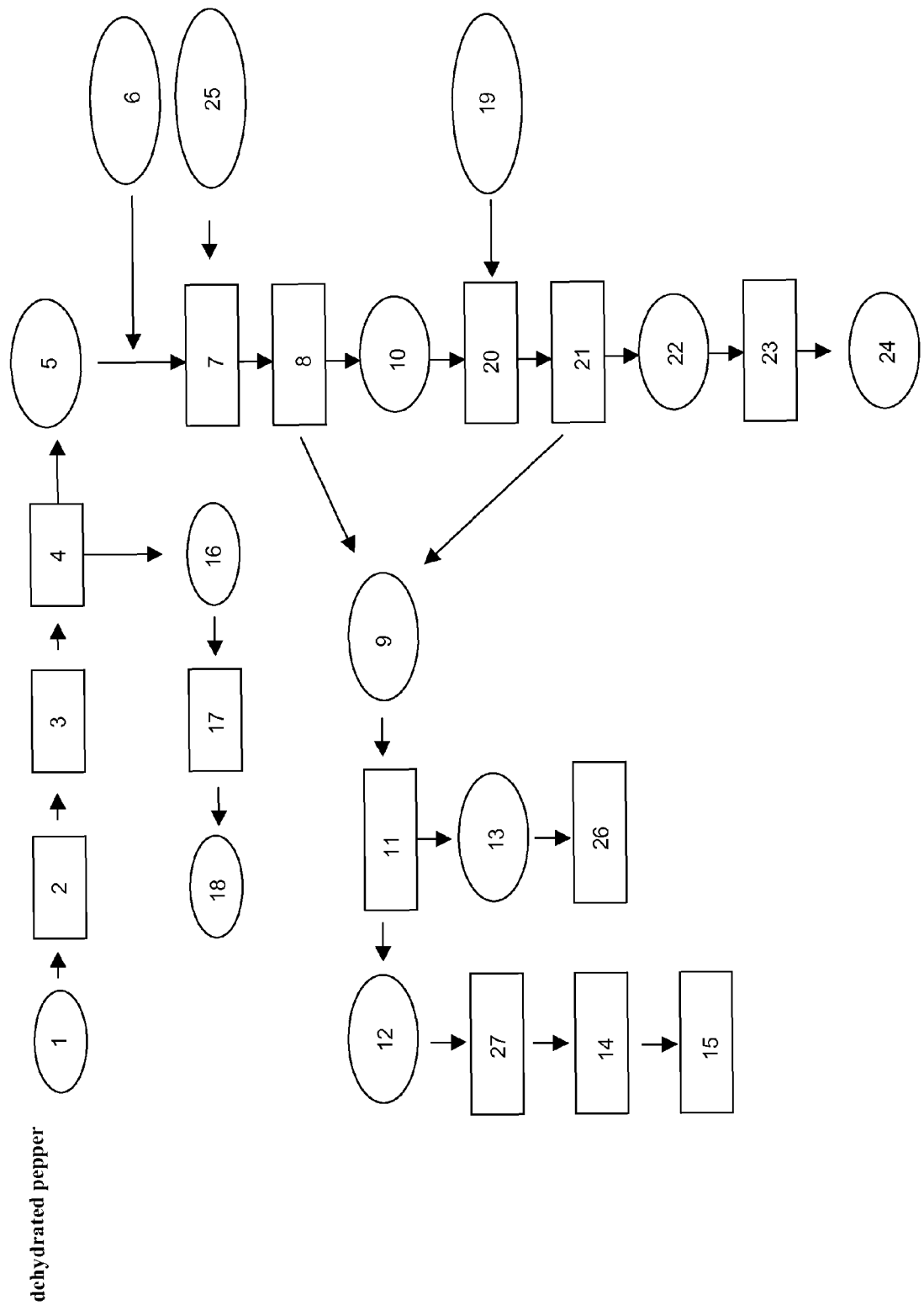

METHOD FOR OBTAINING NATURAL EXTRACTS, OLEORESINS, CONDIMENTS, COLORANTS, FLAVORING SUBSTANCES AND AROMAS FROM AROMATIC PLANT SUBSTANCES, ALFALFA, FLOWERS WITH PIGMENTS, AND VEGETABLES

FIELD OF THE INVENTION

The present invention relates to a method for obtaining natural extracts, oleoresins, colorants, aromas and flavors starting from spices, aromatic herbs, alfalfa, flowers with pigments, carrots, green and red peppers, tomatoes, spinach to and other vegetables containing a natural aromatic active ingredient, colorant or flavoring susceptible of use in human or animal food, in perfumes and in cosmetics, as a raw material.

The invention also provides a method for obtaining paprika with a high concentration of natural pigments starting from pepper freshly picked from the is field by manual or mechanical means, preventing the loss of color and providing the concentration of the natural pigments of fresh pepper to obtain a dehydrated paste with a high concentration of pigments, ideal for obtaining paprika oleoresins by customary methods.

The invention is proposed to prevent the use of organic additives and solvents in methods for obtaining natural extracts, oleoresins, colorants, aromas and flavors, whereby eliminating possible health risks from the residues of organic additives and/or solvents which always remain when an extraction with solvents of this nature is performed.

The quality of the products obtained is also improved because with this invention, the entire process is performed at temperatures below 60° C., whereby the thermolabile components (which decompose due to heat) of these extracts, oleoresins, colorants, aromas and flavors are not altered by the manufacturing process.

BACKGROUND OF THE INVENTION

A well known method for obtaining natural extracts, oleoresins, colorants, aromas and flavors starting from spices, aromatic herbs, alfalfa, flowers with pigments, carrots, green and red peppers, tomatoes, spinach and other vegetables, is based on extraction by means of using organic solvents (hexane, petroleum ether, dichloromethane and other organochlorine solvents, methyl, ethyl, isopropyl alcohols, etc.). High temperatures and other actions are generated in some phases of this extraction process which induce oxidation and the partial or complete destruction of basic components.

In addition, it is virtually impossible to completely remove the residual amounts of the solvents used in obtaining the extracts, oleoresins, colorants, aromas and flavors.

Furthermore, it is generally required that the product to be extracted be dehydrated, whereby since dehydration of the starting product, spices, aromatic herbs, alfalfa, flowers with pigments, carrots, green and red peppers, tomatoes, spinach and other vegetables used must be performed by means of heat and/or air, part of their flavoring, aromatizing or colorant components also oxidize and they are destroyed, with the subsequent reduction of quality.

Patent ES 162248 relates to method for preparing powder or fine-grain conservable products with a high vitamins C content, and for preparing paprika rich in said vitamins, starting from ripe fruits, and comprising the separation of the skin, veins and seeds, preparation of a juice or gruel in a neutral gas atmosphere and reduction to powder by grinding in a heated chamber, mixing said powder with the material resulting from milling the skins, veins and seeds.

Patent ES 476456 discloses a method for directly obtaining sterilized paprika powder or flakes by means of a continuous process by concentration, starting from pepper as a raw material.

Patent ES 482035 describes a method for obtaining paprika from fresh fruit without dehydration by heat, yielding a product suitable for marketing as paprika or as a raw material for oleoresin extraction.

Patent ES 8400228 relates to a method for increasing the value of the inner content of the crude paprika product, which comprises harvesting ripe fruit, separating the stems, grinding the product, centrifuging and/or pressing and drying the product with hot air.

Patent ES 2080685 relates to a method for the non-destructive separation of the chloroplast pigments and the glycerin fraction in vegetable oils and oleoresins which comprises subjecting oleoresin samples to contact with N,N-dialkylamides and performing various decanting steps, separating the hypophases and clustering the epiphases containing pigments for filtering and washing through a sodium sulfate anhydride bed.

However, the methods described in said patents do not solve the oxidation and color loss problems and they do not explain how to directly obtain paprika oleoresin.

Nor do said methods of the state of the art allow concentrating the pigments in the paprika obtained.

DESCRIPTION OF THE INVENTION

The proposed method has been conceived to solve the drawbacks described above, and allows obtaining natural extracts, oleoresins, colorants, aromas and flavors starting from spices, aromatic herbs, alfalfa, flowers with pigments, carrots, green and red peppers, tomatoes, spinach and other vegetables without using organic solvents or having to previously dehydrate the products to be processed.

Starting from the mentioned raw materials, the method of the invention generally comprises the following operating phases:

Washing the fresh agricultural products with sodium hypochlorite diluted in water to obtain a considerable reduction of the content in dirt residues, pesticide residues, fungicide residues, herbicide residues, fertilizer residues, insects, rodent hairs, bacteria, fungi and other unwanted substances.

Rinsing with water.

Gentle milling in a hammer or blade mill to facilitate and increase the performance of the following process.

Sifting the product, whereby separating a first pulp phase with a high water content containing the natural extracts, oleoresins, colorants, aromas and flavors, from a second cellulose phase containing the woody materials, skin, fibers, seed, peduncles etc.

The pulp phase is transferred to fermentation tanks where, by natural fermenting and enzymatic action or an action induced by added enzymes and/or microorganisms, the walls of the microcells which contain the natural extracts, oleoresins, colorants, aromas and flavors, carried in fatty acids, glycerins, phospholipids, resins and other natural fatty substances in the pulp phase, are broken down, leaving such substances free in the pulp phase. In some cases, and to fluidize and better carry the natural extracts, oleoresins, colorants, aromas and flavors, a small amount of a vegetable oil suitable for human consumption is added.

After fermenting the pulp phase, which has a moisture content between approximately 85% and 95%, a first centrifugation process is started, where two phases are obtained: phase A containing water, mineral salts, proteins, carbohydrates and other water-soluble substances, with the natural extracts, oleoresins, colorants, aromas and flavors, carried in fatty acids, glycerins, phospholipids, resins and other natural fatty substances, and phase B, a paste in which the moisture has been reduced to 50%.

Phase (A) then enters a second centrifugation process, where the natural extracts, oleoresins, colorants, aromas and flavors, carried in fatty acids, glycerins, phospholipids, resins and other natural fatty substances, are separated from the water, mineral salts, proteins, carbohydrates and other water-soluble substances. The fractions of natural extracts, oleoresins, colorants, aromas and flavors, carried in fatty acids, glycerins, phospholipids, resins and other natural fatty substances, i.e., the liposoluble phase, are subjected to a pasteurization process to remove microorganisms, whereby the product is ready for standardization and use by means of packaging. In turn, the fractions of water, mineral salts, proteins, carbohydrates and other water-soluble substances can be concentrated by evaporating the water or they are discarded, whichever is appropriate.

Phase B is diluted in water to a moisture content between 85% and 95% and the two preceding steps (first and second centrifugation) are repeated until phase B is virtually free of the natural extracts, oleoresins, colorants, aromas and flavors, leaving a paste, or byproduct 2, with a moisture content less than 50%, which is air dried or dried by an artificial dryer, reducing its moisture content to approximately 12%.

The cellulose phase, or byproduct 1, resulting from the initial sifting, is subjected to an air drying process or is dried by an artificial dryer, reducing its moisture content to approximately 12%.

In one embodiment, the spices, aromatic herbs, alfalfa, flowers with pigments, carrots, green and red peppers, tomatoes, spinach and other vegetables are used in dehydrated form, being rehydrated with water to a proportion of 5 to 8 parts of water for 1 part of the dehydrated product, thus obtaining a pulp phase equivalent to that obtained when sifting the product, the rest of the process continuing as described above.

In the particular case for obtaining paprika, the following operating phases are obtained:

Washing the fresh pepper with sodium hypochlorite diluted in water to obtain a considerable reduction of the content of calcium residues, pesticide or fertilizer residues, insects, rodent hairs and mycopathogens.

Scalding of the previously washed product to facilitate separating skin from the pulp of the pepper and to inactivate lipoxygenase, an enzyme which catalyzes the oxidative decomposition of the pigments. This scalding process will be performed at an approximate temperature of 60° C. for a period of approximately 5 minutes.

In a third phase the product is ground in a hammer mill to increase its contact surface and to facilitate the transport of the raw material and increase the performance of the following process.

After grinding, the product is sifted, separating the pulp of the pepper, which is where all the fat and pigments are concentrated, from the parts of the pepper containing no pigments, with the particularity that this sifting phase on one hand removes the skin, peduncles and seeds containing no pigments (forming a byproduct), milling the pulp to obtain a paste with approximately 85% water, and obtaining a first concentration of pigments.

The byproduct obtained based on the mixture of skin, seeds and peduncles is subjected to an artificial drying process, reducing its moisture content to approximately 12%.

After the sifting phase, the pulp separated from the remaining components or pepper paste is subjected to fermentation in tanks, where a natural decantation of water, proteins, sugars and dissolved salts subsequently takes place, the decanted water in the lower part of the deposits or tanks being removed by means of gravity through a suitable valve, with the particularity that in the decantation and subsequent removal of the dissolved salts, free of pigments, pigments are again concentrated in the product or paprika paste that remains in the tanks having an approximate water content of 85% and a concentrated color.

After the fermentation phase to ferment the pulp, the resulting paste is subjected to centrifugation to obtain two phases, a liquid phase made up of water with dissolved salts and paprika oleoresin, and another phase made up of a paprika paste in which the moisture content has been reduced to 50%; the liquid phase is subjected to another centrifugation in which the water with the dissolved salts is removed and the paprika oleoresin is recovered.

After the fermentation and subsequent centrifugation, the resulting paprika paste is transferred to an artificial drier, where the moisture content is reduced to 10%, obtaining dehydrated paprika in flakes in which the color has been concentrated up to 400% with respect to the raw material used, such that after the described process, the resulting paprika will have up to 16% fat and a high concentration of pigments.

A liquid phase corresponding to water, proteins, sugars, dissolved salts and paprika oleoresins is obtained in the centrifugation phase, said liquid compound being subjected to a second centrifugation process, the water, proteins, sugars and the dissolved salts being removed and paprika oleoresin being separately obtained.

Milled dry pepper or product could be used in one embodiment variant, subsequently hydrating it again until reaching a 5/1 ratio of fresh/dry product, thus obtaining the paste provided in the phase of the sifting process, the process continuing in the same way as described above.

BRIEF DESCRIPTION OF THE DRAWING

The invention will be described below with the aid of a schematic drawing constituting a flow chart of the method, illustrated in the attached FIG. 1.

DETAILED DESCRIPTION OF SEVERAL EMBODIMENTS

Spices, aromatic herbs, alfalfa, flowers with pigments, carrots, green and red peppers, tomatoes, spinach and other vegetables containing a natural aromatic active ingredient, colorant or flavoring are used as raw starting material 1 in the method for obtaining natural extracts, oleoresins, colorants flavors and aromas of the invention, and it comprises the following steps:

a) washing 2 the fresh plant substances 1 for example with sodium hypochlorite diluted in water;
b) rinsing with water;
c) gentle milling 3 in a hammer or blade mill;
d) sifting 4 the product resulting from the milling, yielding:
   d1) a pulp phase 5 with a high water content, containing natural extracts, oleoresins, colorants, aromas and flavors;
   d2) a cellulose phase 16 containing woody materials, skin, fibers, seed, peduncles etc.;
e) transferring the pulp phase 5 to fermentation tanks 7 where a natural fermenting and enzymatic action or an action induced by ferments 6, such as added enzymes and/or microorganisms, takes place; a small amount of vegetable oil 25 suitable for human consumption can optionally be added in said fermentation process.
f) first centrifugation 8 of the fermented pulp phase 5 yielding two phases:
   f1) phase (A), in 9, containing water, mineral salts, proteins, carbohydrates and other water-soluble substances, with natural extracts, oleoresins, colorants, aromas and flavors, carried in fatty acids, glycerins, phospholipids, resins and other natural fatty substances; and
   f2) phase (B), in 10, in the form of a paste in which the moisture has been reduced to 50%.
g) second centrifugation 11 of the mentioned phase (A) which causes the separation of natural extracts, oleoresins, colorants, aromas and flavors, carried in a liposoluble phase 12 containing fatty acids, glycerins, phospholipids, resins and other natural fatty substances, from a water-soluble phase 13 containing water, mineral salts, proteins, carbohydrates and other water-soluble substances.

The mentioned liposoluble phase 12 is subjected to pasteurization 27 and to standardization 14 and packaging 15 processes.

The water-soluble phase 13 is subjected to drying 26 (concentration by evaporating the water), is discarded or eventually fed into a hydration phase 20, which will be explained below.

The cellulose phase 16 or byproduct 1 is dried in 17 by means of an air drying process or by an artificial dryer, reducing its moisture content to approximately 12%, yielding a byproduct 1 or dry cellulose phase 18.

In turn, phase B, 10 is diluted in water (step 20 with supply of water 19) to a moisture content between 85% and 95% and steps f) and g) are repeated (see the arrow leading to step 9) with a first centrifugation 21 until phase B is virtually free of natural extracts, oleoresins, colorants, aromas and flavors, yielding a paste 22, or byproduct 2, with a moisture content less than 50%, which is air dried 23 or dried by an artificial dryer, reducing its moisture content to approximately 12% and yielding a byproduct 2 dry, in 24.

As indicated, it is possible to implement the described method using is spices, aromatic herbs, alfalfa, flowers with pigments, carrots, green and red peppers, tomatoes, spinach and other vegetables in dehydrated form as a starting product, being rehydrated with water to a proportion of 5 to 8 parts of water for 1 part of the dehydrated product, obtaining a pulp phase equivalent to that obtained when sifting the product (step d1)) to which the aforementioned steps d) to g) are applied.

What is claimed is:

1. A method for obtaining natural extracts, oleoresins, condiments, colorants, flavoring substances, and aromas, consisting of the following steps:
   a) washing aromatic plant substances, vegetables or agricultural products with a chemical that is diluted in water and suitable for cleaning;
   b) rinsing or scalding with water at an approximate temperature of 60° C. for about 5 minutes;
   c) milling in a hammer or blade mill;
   d) sifting the product resulting from the milling, which yields:
      d1) a pulp phase with a water content, containing natural extracts, oleoresins, colorants, aromas, and flavors,
      d2) a cellulose phase containing woody materials, skin, fibers, seed, and peduncles;
   e) transferring said pulp phase by using vegetable oil to fluidize the transfer to fermentation tanks where a natural fermenting and enzymatic action takes place to obtain a pulp phase with about 85% to 95% moisture content;
   f) effecting first centrifugation of fermented pulp phase yielding two phases:
      f1) a liquid phase (A) containing water, mineral salts, proteins, carbohydrates, and other water-soluble substances, natural extracts, oleoresins, colorants, aromas, and flavors; and
      f2) a phase (B) in the form of a paste, reducing the moisture content of the paste to 50%; and
   g) effecting second centrifugation of the mentioned phase (A) which causes the separation of natural extracts, oleoresins, colorants, aromas, and flavors in a liposoluble phase into liposoluble fractions from the water, mineral salts, proteins, carbohydrates, and other water-soluble substances; and
   h) diluting phase (B) in water to a moisture content between about 85% to 95% and repeating first centrifugation step until phase (B) is free of natural extracts, oleoresins, colorants, aromas, and flavors.

2. The method according to claim 1, wherein the liposoluble phase gives rise to liposoluble fractions of natural extracts, oleoresins, colorants, aromas and flavors of phase (A).

3. The method according to claim 1, wherein said washing with a chemical that is diluted in water and suitable for cleaning of step a) is performed with sodium hypochlorite diluted in water.

4. A method for obtaining natural extracts, oleoresins, condiments, colorants, flavoring substances and aromas; the method consisting of
   providing a starting product in dehydrated form of spices, aromatic herbs, alfalfa, flowers with pigments, carrots, green peppers, red peppers, tomatoes, spinach, and other vegetables;
   rehydrating with water up to a proportion of 5 to 8 parts of water for 1 part of the dehydrated form of the starting product;
   obtaining a pulp phase;
   transferring said pulp phase by using vegetable oil to fluidize the transfer to fermentation tanks where a natural fermenting and enzymatic action takes place to obtain a pulp phase with about 85% to 95% moisture content;
   effecting first centrifugation of fermented pulp phase yielding two phases:

a liquid phase (A) containing water, mineral salts, proteins, carbohydrates and other water-soluble substances, natural extracts, oleoresins, colorants, aromas, and flavors; and a phase (B) in the form of a paste, reducing the moisture content of the paste to 50%; and effecting second centrifugation of the mentioned phase (A) which causes the separation of natural extracts, oleoresins, colorants, aromas and flavors in a liposoluble phase from the water, mineral salts, proteins, carbohydrates, and other water-soluble substances; and diluting phase (B) in water to a moisture content between about 85% to 95% and repeating first centrifugation step until phase (B) is free of natural extracts, oleoresins, colorants, aromas, and flavors.

5. The method according to claim 1, wherein the vegetable washed is pepper; where the washed pepper is scalded prior to the milling step to separate skin from pulp and to inactivate lipoxygenase at the approximate temperature of 60° C. for a period of approximately 5 minutes, and after the fermentation in tanks where a decantation of water takes place, a paprika paste is obtained in said phase (B), which is dried to obtain paprika with a concentration of pigments.

6. A method for obtaining natural extracts, oleoresins, condiments, colorants, flavoring substances and aromas; the method consisting of:

providing a starting product of dehydrated pepper;

separating seeds from the dehydrated pepper, being ground and then milled, then being hydrated with water to obtain a pepper paste which is used as pepper pulp;

transferring said pulp phase by using vegetable oil to fluidize the transfer to fermentation tanks where a natural fermenting and enzymatic action takes place to obtain a pulp phase with about 85% to 95% moisture content;

effecting first centrifugation of fermented pulp phase yielding two phases:

a liquid phase (A) containing water, mineral salts, proteins, carbohydrates and other water-soluble substances, natural extracts, oleoresins, colorants, aromas and flavors; and a phase (B) in the form of a paste, reducing the moisture content of the paste to 50%; and effecting second centrifugation of the mentioned phase (A) which causes the separation of natural extracts, oleoresins, colorants, aromas and flavors in liposoluble phase from the water, mineral salts, proteins, carbohydrates and other water-soluble substances; and diluting phase (B) in water to a moisture content between about 85% to 95% and repeating first centrifugation step until phase (B) is free of natural extracts, oleoresins, colorants, aromas and flavors.

7. A method for obtaining natural extracts, oleoresins, condiments, colorants, flavoring substances and aromas, consisting of the following steps:

a) washing aromatic plant substances, vegetables, or agricultural products;

b) rinsing with water at an approximate temperature of 60° C. for about 5 minutes;

c) milling in a hammer or blade mill;

d) sifting the product resulting from the milling which yields:

d1) a pulp phase with a water content, containing natural extracts, oleoresins, colorants, aromas, and flavors, d2) a cellulose phase containing woody materials, skin, fibers, seed, and peduncles;

e) transferring said pulp phase by using vegetable oil to fluidize the transfer to fermentation tanks where an action induced by added enzymes and/or microorganisms takes place to obtain a pulp phase with about 85% to 95% moisture content, f) effecting first centrifugation of fermented pulp phase yielding two phases:

f1) a liquid phase (A) containing water, mineral salts, proteins, carbohydrates, and other water-soluble substances, and natural extracts, oleoresins, colorants, aromas, and flavors; and f2) a phase (B) in the form of a paste, reducing the moisture content of the paste to 50%; and g) effecting second centrifugation of the mentioned phase (A) which causes the separation of natural extracts, oleoresins, colorants, aromas, and flavors in a liposoluble phase, from the water, mineral salts, proteins, carbohydrates, and other water-soluble substances: and h) diluting phase (B) in water to a moisture content between about 85% to 95% and repeating first centrifugation step until phase (B) is free of natural extracts, oleoresins, colorants, aromas and flavors.

* * * * *